United States Patent
Drobyshev et al.

(10) Patent No.: US 10,604,456 B2
(45) Date of Patent: Mar. 31, 2020

(54) METHOD FOR DEHYDRATING ALCOHOLS INTO OLEFINS COMPRISING THE RECYCLING OF ALCOHOLS

(71) Applicants: TOTAL RESEARCH & TECHNOLOGY FELUY, Seneffe (BE); IFP Energies nouvelles, Rueil-Malmaison (FR)

(72) Inventors: Kirill Drobyshev, Rueil-Malmaison (FR); Vincent Coupard, Villeurbanne (FR); Jean-Christophe Gabelle, Crolles (FR); Nikolai Nesterenko, Nivelles (BE); Christophe Thille, Charleroi (BE)

(73) Assignees: TOTAL RESEARCH & TECHNOLOGY FELUY, Seneffe (BE); IFP Energies nouvelles, Rueil-Malmaison (FR)

( * ) Notice: Subject to any disclaimer, the term of this patent is extended or adjusted under 35 U.S.C. 154(b) by 1 day.

(21) Appl. No.: 16/134,363

(22) Filed: Sep. 18, 2018

(65) Prior Publication Data
US 2019/0084901 A1    Mar. 21, 2019

(30) Foreign Application Priority Data
Sep. 19, 2017   (FR) ...................... 17 58667

(51) Int. Cl.
C07C 1/24     (2006.01)
C07C 7/04     (2006.01)
B01J 29/65    (2006.01)
B01D 3/14     (2006.01)
C07C 5/27     (2006.01)

(52) U.S. Cl.
CPC .................. *C07C 1/24* (2013.01); *B01D 3/14* (2013.01); *B01J 29/65* (2013.01); *C07C 5/2775* (2013.01); *C07C 7/04* (2013.01); *C07C 2529/65* (2013.01); *C07C 2529/88* (2013.01)

(58) Field of Classification Search
CPC .......... C07C 1/24; C07C 5/2775; C07C 7/04; C07C 2529/65; C07C 2529/88; B01J 29/65; B01D 3/14
See application file for complete search history.

(56) References Cited

U.S. PATENT DOCUMENTS
10,099,969 B2    10/2018   Vivien

FOREIGN PATENT DOCUMENTS

| EP | 3162763 A1 | 5/2017 | |
|----|------------|--------|---|
| FR | 3026406 A1 * | 4/2016 | ............. B01J 29/65 |
| WO | 2011085223 A1 | 7/2011 | |
| WO | 2016046242 A1 | 3/2016 | |

OTHER PUBLICATIONS

Search Report in corresponding FR application 1758667 dated Jun. 5, 2018 (pp. 1-4).

* cited by examiner

*Primary Examiner* — In Suk C Bullock
*Assistant Examiner* — Jason Y Chong
(74) *Attorney, Agent, or Firm* — Millen White Zelano and Branigan, PC; Csaba Henter

(57) ABSTRACT

This invention relates to a method for dehydration of alcohols into olefins comprising an improved step for recovery of unreacted alcohol.

6 Claims, No Drawings

METHOD FOR DEHYDRATING ALCOHOLS INTO OLEFINS COMPRISING THE RECYCLING OF ALCOHOLS

TECHNICAL FIELD OF THE INVENTION

This invention relates to a method for dehydration of alcohols into olefins comprising an improved step for recovery of unreacted alcohol. The feedstock of the method can be obtained by chemical methods or by fermentation methods.

The alkenes obtained—in particular isobutene, butene-1, and butenes-2—have an important advantage in the field of the petrochemical industry and organic synthesis.

PRIOR ART

The document EP 2348 005 describes the dehydration of alcohols containing 2 to 10 carbon atoms into the olefin corresponding to a zeolitic catalyst FER of an Si/Al atomic ratio of less than 100. The weight hourly space velocity (Weight Hourly Space Velocity according to the English designation, or WHSV) in relation to alcohol is at least 4 h$^{-1}$, and the temperature is from 320 to 600° C.

The document WO 2011/113834 describes the dehydration and simultaneous skeletal isomerization of isobutanol in the presence of crystalline silicate catalysts, of medium channel size (10 MR), dealuminized or not, modified with phosphorus or not, of the group FER, MWW, EUO, MFS, ZSM-48, MTT, MFI, MEL or TON having an Si/Al ratio of greater than 10, silicoaluminophosphate molecular sieves of the group AEL, or silica-, zirconia-, titanium- or fluorine-alumina on zeolitic catalysts. The PPH (ratio of the mass flow rate of the feedstock to the catalyst mass, corresponding to the WHSV) in relation to the alcohol is at least 1 h$^{-1}$, and the temperature is from 200 to 600° C. The maximum proportion reached of n-butenes in butenes is 58.4% at 375° C. with high PPH (12.6 h$^{-1}$) in a powder FER zeolite of Si/Al 33.

So as to continue to achieve the goal in terms of conversion, the mean reaction temperature is increased, creating drops in selectivity. The recovery and recycling of the unreacted reactive radicals is therefore of prime importance for the viability of the method.

The applicant discovered a particular arrangement of the alcohol dehydration method, making possible a better recovery and recycling of unreacted alcohol, thus making possible a better overall conversion.

OBJECT AND ADVANTAGE OF THE INVENTION

The invention relates to a method for isomerizing dehydration of a feedstock comprising 40 to 100% by weight of primary alcohol substituted in position 2 by an alkyl group comprising at least the following steps:

a) Pressurization of said feedstock, followed by the mixing of a fraction of said feedstock, compressed, with the alcohol-rich organic effluent obtained from step h) and with a fraction of the aqueous effluent obtained from step f), and then preheating of said mixture by heat exchange, advantageously with an olefinic effluent obtained from step g), with an aqueous effluent coming from step f) and with a dehydration effluent obtained from step c) in such a way as to produce a partially vaporized feedstock, with the residual compressed feedstock fraction being sent to step h);

b) Vaporization and final superheating of said partially vaporized feedstock at a temperature of between 250 and 375° C. in such a way as to produce a vaporized feedstock;

c) Dehydration of said vaporized feedstock in at least one dehydration reactor that operates in the gas phase at a weighted mean temperature of between 250 and 375° C., at a pressure of between 0.2 MPa and 1 MPa, and at a PPH of between 1 and 18 h$^{-1}$, in the presence of a catalyst that comprises a zeolite that has at least one series of channels whose opening is defined by a ring with 8 oxygen atoms (8 MR), with said catalyst being coked in advance in-situ or ex-situ, in such a way as to produce a dehydration effluent;

d) Cooling of said dehydration effluent obtained from step c) to a temperature of between 30 and 50° C., advantageously by at least four successive indirect heat exchanges with at least said feedstock of step a), with the organic and aqueous phases obtained from step e) and a cold utility, in such a way as to produce a cooled effluent;

e) Separation by decanting of said cooled effluent into an aqueous phase and an organic phase;

f) Separation by distilling of said aqueous phase obtained from step e) in such a way as to produce a light hydrocarbon effluent and an aqueous effluent, with a fraction of said aqueous effluent being purged, and the other part being recycled to step a);

g) Separation by distilling of said organic phase obtained from step e) in such a way as to produce an olefinic effluent and a heavy hydrocarbon effluent;

h) Mixing of the heavy hydrocarbon effluent obtained from step g) with the residual compressed feedstock fraction obtained from step a), with the flow rate of said residual fraction being adjusted in such a way that the ratio by mass of the flow rates of said residual fraction to unconverted alcohol in said heavy hydrocarbon effluent is between 2:1 and 10:1, and then separation by distilling of said mixture in such a way as to produce a $C_5$-$C_6$ hydrocarbon effluent, an alcohol-rich organic effluent, and a $C_6$+ hydrocarbon effluent, and recycling of said alcohol-rich organic effluent to step a).

Light hydrocarbon effluent is defined as an effluent that comprises for the most part hydrocarbons comprising at most 4 carbon atoms, i.e., at least 50% by weight of hydrocarbons comprising at most 4 carbon atoms.

Olefinic effluent is defined as an effluent that comprises at least 50% by weight, advantageously at least 70% by weight, preferably at least 80% by weight, of olefins corresponding to primary alcohol(s) substituted in position 2 by an alkyl group fed into the feedstock of the method according to the invention.

Heavy hydrocarbon effluent is defined as an effluent that comprises at least 50% by weight of hydrocarbons comprising at least 4 carbon atoms, advantageously at least 5 carbon atoms.

The purpose of the method according to the invention is to produce primarily linear olefins in an olefinic effluent obtained from step g), with said linear olefins being the olefins corresponding to the primary alcohol(s) substituted in position 2 by an alkyl group fed into the feedstock of the method according to the invention, and to recycle the unconverted alcohol obtained following a dilution of a heavy hydrocarbon phase by the alcohol of the feedstock and a distillation of said mixture.

One advantage of the method according to the invention is, by a dilution of the heavy hydrocarbon effluent obtained from step g), to improve the recovery of unreacted alcohol by improving the purity of the recycled alcohol-rich organic effluent.

In addition to a better recovery, this arrangement limits the accumulation of impurities in the recycling loop, which prevents or reduces the necessary purges in said loops, therefore improving the overall yield of the method.

DETAILED DESCRIPTION OF THE INVENTION

In accordance with the invention, the method according to the invention is a method for isomerizing dehydration of a feedstock comprising 40 to 100% by weight of primary alcohol substituted in position 2 by an alkyl group.

The feedstock that is treated in the method according to the invention is a feedstock comprising at least one alcohol, advantageously at least one primary monoalcohol of formula R—CH$_2$—OH, in which R is a non-linear alkyl radical of general formula C$_n$H$_{2n+1}$, where n is an integer of between 3 and 20, preferably between 3 and 10, in a preferred manner between 3 and 5.

The feedstock comprises 40 to 100% by weight, preferably 70 to 100% by weight, in an advantageous manner 85 to 100% by weight, of at least one alcohol, advantageously at least one primary monoalcohol as defined above.

Among the primary monoalcohols that can be used in the method according to the invention, it is possible to cite isobutanol, 2-methylbutan-1-ol, 2,2-dimethylpropan-1-ol, 2-methylpentan-1-ol, 2,2-dimethylbutan-1-ol, 2-ethylbutan-1-ol. Said feedstock can comprise one or more primary monoalcohols.

Said primary monoalcohol is preferably isobutanol or 2-methyl-1-butanol, taken by itself or in a mixture. Very preferably, said primary monoalcohol is isobutanol.

Said feedstock can be obtained from chemical or biochemical methods, for example fermentation methods. In particular, this feedstock can be obtained from methods for fermenting lignocellulosic biomass.

Said feedstock can contain water, advantageously up to 15% by weight of water, preferably up to 10% by weight, very advantageously up to 5% by weight. It can also comprise impurities of mineral type (such as Na, Ca, P, Al, Si, K, SO$_4$) and of organic type (such as methanol, ethanol, n-butanol, aldehydes, ketones, and corresponding acids, for example furanic acid, acetic acid, isobutyric acid).

Step a) for Preheating

In accordance with the invention, the method according to the invention comprises a step for pressurization of said feedstock, followed by the mixing of a fraction of said feedstock, compressed, with the alcohol-rich organic effluent obtained from step h) and with a fraction of the aqueous effluent obtained from step f), then preheating of said mixture by heat exchange, advantageously with an olefinic effluent obtained from step g), with an aqueous effluent obtained from step f) and with a dehydration effluent obtained from step c) in such a way as to produce a partially vaporized feedstock, with the residual compressed feedstock fraction being sent to step h).

The pressurization can be carried out by any means known to one skilled in the art, in particular using a pump.

Said feedstock is pressurized at a pressure of between 0.2 and 1 MPa. Said preheating makes it possible for said mixture to reach a temperature of between 100 and 250° C., preferably between 100 and 200° C.

The residual compressed feedstock fraction is sent to step h) mixed with the heavy hydrocarbon effluent obtained from step g), with the flow rate of said residual fraction being adjusted in such a way that the ratio by mass of the flow rates of residual fraction to unconverted alcohol in a heavy hydrocarbon effluent is between 2:1 and 10:1.

Unconverted alcohol flow rate in a heavy hydrocarbon effluent is defined as the flow rate in the heavy hydrocarbon effluent obtained from step g) for primary mono-alcohol of formula R—CH$_2$—OH, in which R is a non-linear alkyl radical of general formula C$_n$H$_{2n+1}$, where n is an integer of between 3 and 20, preferably between 3 and 10, in a preferred manner between 3 and 5, preferably an alcohol selected from the group that consists of isobutanol, 2-methylbutan-1-ol, 2,2-dimethylpropan-1-ol, 2-methylpentan-1-ol, 2,2-dimethylbutan-1-ol, 2-ethylbutan-1-ol, and mixtures thereof, very preferably in the group that consists of isobutanol, 2-methyl-1-butanol, and mixtures thereof and in a very preferred manner isobutanol.

Step b) for Vaporization and Superheating

In accordance with the invention, the method according to the invention comprises a step b) of vaporization and final superheating of said partially vaporized feedstock obtained from step a) in such a way as to produce a vaporized feedstock.

In an advantageous manner, said partially vaporized feedstock obtained from step a) is vaporized by at least one indirect exchange with a hot utility, and then superheated by an indirect exchange with a hot utility. Said feedstock is superheated to a temperature of between 250 and 375° C., preferably between 310 and 365° C.

Step c) for Dehydration

In accordance with the invention, the method according to the invention comprises a step for dehydrating said vaporized feedstock in at least one dehydration reactor operating in the gas phase at a weighted mean temperature of between 250 and 375° C., at a pressure of between 0.2 MPa and 1 MPa, and at a PPH of between 1 and 18 h–1, in the presence of a catalyst comprising a zeolite having at least one series of channels whose opening is defined by a ring with 8 oxygen atoms (8 MR), with said catalyst being coked in advance in-situ or ex-situ, in such a way as to produce a dehydration effluent.

The dehydration step comprises at least one dehydration reactor. When this step comprises more than one reactor, the temperature at the inlet of each of the reactors is adjusted to a value of between 250 and 375° C. by a heating means, as the isomerizing dehydration reaction being endothermic, and each reactor is operated under identical conditions. Thus, in the disclosure below, the term "the reactor" refers both to the reactor of said step c), when the latter comprises only one reactor, and to each of the reactors of said step c), when the latter comprises more than one reactor.

The reactor is operated in the gas phase, at a weighted mean temperature of between 250 and 375° C., at a pressure of between 0.2 MPa and 1 MPa, at a PPH of between 1 and 18 h–1, in the presence of a catalyst comprising a zeolite comprising at least one series of channels whose opening is defined by a ring with 8 oxygen atoms (8 MR). Said catalyst is placed in one or more fixed beds, which can be operated in upward, downward or radial flow.

PPH is defined as "weight by weight by hour," i.e., the mass flow rate of primary alcohol substituted in position 2 by an alkyl group in the feedstock at the reactor inlet divided by the catalyst mass in said reactor. This concept is also sometimes referred to under its English acronym of WHSV, or "Weight Hourly Space Velocity."

Weighted mean temperature is defined as the mean of the temperature in the catalytic bed calculated along the flow axis in said bed. For a bed of length L and surface S, and with the reactive mixture flowing along the longitudinal axis x of this bed and the intake in the catalytic bed forming the origin of the axis (x=0), the weighted mean temperature is expressed according to:

$$TMP = \frac{1}{L}\int_0^L T(x)dx$$

In accordance with the invention, the catalyst that is used in said dehydration reaction step comprises a zeolite having at least one series of channels whose opening is defined by a ring with 8 oxygen atoms (8 MR) as defined in the classification "Atlas of Zeolite Structure Types," Ch. Baerlocher, L. B. McCusker, D. H. Olson, 6$^{th}$ Edition, Elsevier, 2007, Elsevier.

According to a particular embodiment, the zeolite can also advantageously contain at least one series of channels whose opening of pores is defined by a ring containing 10 oxygen atoms (10 MR).

Said zeolite is advantageously selected from among the zeolites having 8 and 10 MR channels such as the FER- and MFS-structural-type zeolites, taken by themselves or in a mixture. The zeolite is more advantageously selected from the group that consists of, for the FER type, the zeolites ferrierite, FU-9, ISI-6, NU-23, ZSM-35, and for the MFS type, the zeolite ZSM-57, and mixtures thereof. Said zeolite is very advantageously of the FER type, and preferably ferrierite. Preferably, said zeolite consists of ferrierite.

In a preferred way, said zeolite is a ferrierite with an Si/Al molar ratio of 8 to 70, preferably 10 to 70, preferably selected between 10 and 50, and in a preferred manner selected between 20 and 50.

Said catalyst also comprises a binder.

The zeolite content in the catalyst is 55-90% by weight, preferably between 60 and 80% by weight.

The binder is advantageously selected from among a silicic binder, an AlPO4, a clay, a zirconia, a Ti oxide, a SiC. In a very preferred way, it is a silicic binder.

The binder content in the catalyst is between 10 and 45% by weight, preferably between 20 and 40%. The catalyst can optionally contain impurities, small in quantity, that have not technical effect on the conversion/selectivity of the catalyst. Said catalyst can be shaped by any of the techniques known to one skilled in the art, for example in the form of powder, balls, pellets, granules, or extrudates (cylinders that may or may not be hollow, multilobed cylinders with 2, 3, 4 or 5 lobes for example, twisted cylinders), rings, etc.

Generally, the catalyst comprises no metals. This expression "no metals" means that there are no metals added during the preparation. It further means that there may be impurities in the binders and therefore in small amounts. In a preferred manner, there is no aluminum or iron in the silica.

Said reaction step c) is a step in which alcohol is dehydrated into olefins, with the branched alcohols advantageously being dehydrated into linear olefins. Said reaction step of the method according to the invention is advantageously an isomerizing dehydration step.

Step d) for Cooling

In accordance with the invention, the method according to the invention comprises a step for cooling of said dehydration effluent, advantageously by at least four successive indirect heat exchanges with at least said feedstock obtained from step a), the organic and aqueous phases obtained from step e), and a cold utility, in such a way as to produce a cooled effluent.

Said cooling step makes it possible to cool said dehydration effluent to a temperature of between 30 and 50° C., preferably between 35 and 45° C. This cooling temperature makes it possible, on the one hand, to liquefy the dehydration effluent, and, on the other hand, to achieve the separation of the liquefied effluent into an aqueous phase and an organic phase, with this temperature range making it possible to maximize the recovery of alkene and alcohol.

Step e) for Decanting

In accordance with the invention, the method according to the invention comprises a step for separation by decanting of said cooled effluent obtained from step d) into an aqueous phase and an organic phase.

This step can be implemented by any means known to one skilled in the art, for example in a decanting tank, with the aqueous phase being drawn off in the lower part and the organic phase in the upper part.

Step f) for Treating an Aqueous Phase

In accordance with the invention, the method according to the invention comprises a step for separation by distilling of said aqueous phase obtained from step e) in such a way as to produce a light hydrocarbon effluent and an aqueous effluent, with a fraction of said aqueous effluent being purged, and the other part being recycled to step a).

The fraction of the aqueous effluent that is recycled to step a) represents between 10 and 20% by weight of the flow rate of the aqueous phase obtained from step e), advantageously between 12 and 17% by weight. Said separation step is carried out at a pressure of between 0.8 and 0.9 MPa.

The fraction of the aqueous effluent recycled to step a) is adjusted in such a way that the water content in the vaporized feedstock at the inlet of step c) is between 4 and 15% by weight, advantageously between 4 and 10% by weight, and very advantageously between 5 and 10% by weight.

Step g) for Separation

In accordance with the invention, the method according to the invention comprises a step for separation by distilling the organic phase obtained from step e) in such a way as to produce an alkene effluent and a heavy hydrocarbon effluent.

Said distillation is implemented in at least one distillation column, carried out at a pressure of between 0.6 and 0.7 MPa. This distillation, known to one skilled in the art, is carried out according to the rules of the art.

Step h) for Separation of Unconverted Alcohol and for Recycling Alcohol

In accordance with the invention, the method according to the invention comprises a step comprising the mixing of the heavy hydrocarbon effluent obtained from step g) with the residual compressed feedstock fraction obtained from step a), with the flow rate of said residual fraction being adjusted in such a way that the ratio by mass of the flow rates of residual fraction to the unconverted alcohol in a heavy hydrocarbon effluent is between 2:1 and 10:1, and then the separation by distilling of said mixture in such a way as to produce a C5-C6 hydrocarbon effluent, an alcohol-rich organic effluent, and a C6+ hydrocarbon effluent, and recycling of said alcohol-rich organic effluent to step a).

The ratio by mass of the flow rates of residual fraction to unconverted alcohol in the heavy hydrocarbon effluent is advantageously between 5:1 and 9:1. This dilution makes it possible to obtain an alcohol-rich organic effluent comprising between 47 mol % and 92 mol % of alcohol, preferably between 79 mol % and 91 mol % of alcohol, and an overall recovery of alcohol in this step (ratio of the mass flow rate of alcohol in the alcohol-rich organic effluent to the mass flow rate of alcohol in the heavy hydrocarbon effluent) of between 92 and 96%, advantageously between 94 and 96%.

The dilution of the heavy hydrocarbon effluent with a fraction of the feedstock is counter-intuitive because it leads a priori to the pollution of a fraction of the feedstock by bringing it into contact with an effluent comprising numerous impurities, whereas this feedstock should be fed directly into the reaction step, after preheating and vaporization. However, it was observed that the observed increase in the purity of the alcohol-rich organic effluent made it possible to compensate for this pollution effect, on the one hand by an improvement in the recovery of the unreacted alcohol, and, on the other hand, by the reduction of purges required for the recycling loop of said alcohol-rich organic effluent.

EXAMPLES

Example 1 (Non-Compliant)

Recycling of Isobutanol without Dilution Relative to Isobutanol of the Feedstock A heavy hydrocarbon effluent feeds a distillation column in which it is separated into an isobutanol-rich organic effluent, extracted by a lateral draw-off, into a C5-C6 hydrocarbon effluent at the top, and a C6+ hydrocarbon effluent at the bottom. The flow rate of said lateral draw-off is adjusted to extract 95% of the isobutanol that feeds the column. The composition of said lateral draw-off is presented in Table 1.

TABLE 1

Composition of the Isobutanol-Rich Organic Effluent

| Mol % | |
|---|---|
| Isobutanol | 22.65 |
| Acetic Acid | 11.37 |
| 2-Methyl-2-butene | 0.77 |
| Isobutaldehyde | 0.07 |
| n-Butanol | 0.10 |
| s-Butanol | 0.38 |
| t-Butanol | 0.05 |
| 2,3,3-Trimethyl-1-butene | 0.25 |
| 2,4,4-Trimethyl-1-pentene | 63.02 |

Example 2

Recycling of Isobutanol with 2/1 Dilution with Isobutanol of the Feedstock

This example differs from Example 1 in that the heavy hydrocarbon effluent is diluted by a fraction of the feedstock before being separated.

A heavy hydrocarbon effluent feeds a distillation column. Prior to it being fed in, it is diluted with a fraction of the feedstock of the method with a ratio of mass flow rates of feedstock fraction/isobutanol in heavy hydrocarbons effluent that is equal to 2/1. This mixture is separated into an isobutanol-rich organic effluent, extracted by a lateral draw-off, into a C5-C6 hydrocarbon effluent at the top, and a C6+ hydrocarbon effluent at the bottom. The flow rate of said lateral draw-off is adjusted to extract 95% of the isobutanol that feeds the column. The composition of said draw-off is presented in Table 2.

TABLE 2

Composition of the Isobutanol-Rich Organic Effluent

| Mol % | |
|---|---|
| Isobutanol | 47.18 |
| Acetic Acid | 5.76 |
| 2-Methyl-2-butene | 0.68 |
| Isobutaldehyde | 0.06 |
| n-Butanol | 0.08 |
| s-Butanol | 0.24 |
| t-Butanol | 0.04 |
| 2,3,3-Trimethyl-1-butene | 0.79 |
| 2,4,4-Trimethyl-1-pentene | 44.28 |

It is observed that the concentration in isobutanol in the lateral draw-off is improved in relation to Example 1.

Example 3

Recycling of Isobutanol with 10/1 Dilution with Isobutanol of the Feedstock

This example differs from Example 1 in that the heavy hydrocarbon effluent is diluted by a fraction of the feedstock before being separated.

A heavy hydrocarbon effluent feeds a distillation column. Prior to it being fed in, it is diluted with a fraction of the feedstock of the method with a ratio of mass flow rates of feedstock fraction/isobutanol in a heavy hydrocarbon effluent that is equal to 10/1. This mixture is separated into an isobutanol-rich organic effluent, extracted by a lateral draw-off, into a C5-C6 hydrocarbon effluent at the top and a C6+ hydrocarbon effluent at the bottom. The flow rate of said lateral draw-off is adjusted to extract 95% of the isobutanol encompassed in the feed to the column. The composition of said draw-off is presented in Table 3.

TABLE 3

Composition of the Isobutanol-Rich Organic Effluent

| Mol % | |
|---|---|
| Isobutanol | 92.39 |
| Acetic Acid | 1.14 |
| 2-Methyl-2-butene | 0.40 |
| Isobutaldehyde | 0.04 |
| n-Butanol | 0.03 |
| s-Butanol | 0.14 |
| t-Butanol | 0.02 |
| 2,3,3-Trimethyl-1-butene | 0.27 |
| 2,4,4-Trimethyl-1-pentene | 3.37 |

It is observed that the concentration in isobutanol in the lateral draw-off is improved in relation to Example 1.

The invention claimed is:

1. A method for simultaneously dehydrating and isomerizing a feedstock comprising 40 to 100% by weight of a primary alcohol substituted in position 2 by an alkyl group, the method comprising:

a) compressing said feedstock, mixing a fraction of said compressed feedstock with an alcohol-rich organic effluent obtained from step h) and with a fraction of an aqueous effluent obtained from step f) to obtain a feedstock mixture, and then preheating said feedstock mixture to produce a partially vaporized feedstock and a residual compressed feedstock, wherein the residual compressed feedstock fraction is sent to step h);

b) superheating said partially vaporized feedstock at a temperature of between 250 and 375° C. in such a way as to produce a vaporized feedstock;

c) dehydrating said vaporized feedstock in at least one dehydration reactor operating in gas phase at a weighted mean temperature of between 250 and 375° C., at a pressure of between 0.2 MPa and 1 MPa, and at a WHSV of between 1 and 18 h$^{-1}$, in the presence of a catalyst, to produce a dehydration effluent, wherein said catalyst comprises a zeolite having at least one series of channels with a pore opening defined by a ring with 8 oxygen atoms (8 MR) and wherein said catalyst is coked in advance in-situ or ex-situ;

d) cooling said dehydration effluent obtained from step c) to a temperature of between 30 and 50° C. to produce a cooled effluent;

e) separating said cooled effluent by decanting into an aqueous phase and an organic phase;

f) distilling said aqueous phase obtained from step e) to produce a light hydrocarbon effluent and an aqueous effluent, wherein the light hydrocarbon effluent comprises at least 50% by weight of hydrocarbons comprising at most 4 carbon atoms, and wherein a part of said aqueous effluent is purged and another part of said aqueous effluent is recycled to step a);

g) distilling said organic phase obtained from step e) to produce an olefinic effluent and a heavy hydrocarbon effluent, wherein said olefinic effluent comprises at least 50% by weight of olefins corresponding to said primary alcohol(s) substituted in position 2 by an alkyl group and wherein said olefins comprise linear olefins; and h) mixing the heavy hydrocarbon effluent obtained from step g) with the residual compressed feedstock fraction obtained from step a) at a ratio by mass of flow rates of the residual compressed feedstock fraction to unconverted alcohol(s) in the heavy hydrocarbon effluent of between 2:1 and 10:1 to produce a heavy effluent mixture, and then distilling said heavy effluent mixture to produce a C5-C6 hydrocarbon effluent, an alcohol-rich organic effluent comprising unconverted alcohol(s), and a C6+hydrocarbon effluent and recycling said alcohol-rich organic effluent to step a).

2. The method according to claim 1, in which the preheating in step a) is carried out by heat exchange with the olefinic effluent obtained from step g), with the aqueous effluent obtained from step f), and with the dehydration effluent obtained from step c).

3. The method according to claim 1, in which said partially vaporized feedstock is superheated in step b) to a temperature of between 310 and 365° C.

4. The method according to claim 1, in which the zeolite of the catalyst in step c) further comprises at least one series of channels with a pore opening defined by a ring containing 10 oxygen atoms.

5. The method according to claim 1, in which the cooling in step d) is carried out by at least four successive indirect heat exchanges with at least said feedstock of step a), the organic and aqueous phases obtained from step e), and a cold utility.

6. The method according to claim 1, in which the heavy hydrocarbon effluent is mixed with the residual compressed feedstock fraction in step h) at the ratio by mass of the flow rates of the residual compressed feedstock fraction to unconverted alcohol(s) in the heavy hydrocarbon effluent of between 5:1 and 9:1.

* * * * *